US008639011B2

(12) United States Patent
Watanabe

(10) Patent No.: US 8,639,011 B2
(45) Date of Patent: Jan. 28, 2014

(54) FLUOROSCOPY APPARATUS

(75) Inventor: Toshiaki Watanabe, Tokyo (JP)

(73) Assignee: Olympus Corporation, Tokyo (JP)

(*) Notice: Subject to any disclaimer, the term of this patent is extended or adjusted under 35 U.S.C. 154(b) by 0 days.

(21) Appl. No.: 13/599,298

(22) Filed: Aug. 30, 2012

(65) Prior Publication Data

US 2012/0328175 A1 Dec. 27, 2012

Related U.S. Application Data

(63) Continuation of application No. PCT/JP2011/053206, filed on Feb. 16, 2011.

(30) Foreign Application Priority Data

Mar. 23, 2010 (JP) ................. 2010-067019

(51) Int. Cl.
G06K 9/00 (2006.01)
(52) U.S. Cl.
USPC .......................................... 382/132
(58) Field of Classification Search
None
See application file for complete search history.

(56) References Cited

U.S. PATENT DOCUMENTS

| 4,907,156 | A | * | 3/1990 | Doi et al. ...................... 382/130 |
| 5,708,693 | A | * | 1/1998 | Aach et al. .................... 378/62 |
| 5,982,916 | A | * | 11/1999 | Kuhn ........................... 382/132 |
| 8,270,689 | B2 | * | 9/2012 | Liang et al. ................... 382/128 |
| 8,295,917 | B2 | * | 10/2012 | Ishihara ........................ 600/477 |
| 2002/0168096 | A1 | * | 11/2002 | Hakamata et al. ............. 382/132 |
| 2007/0201130 | A1 | | 8/2007 | Fujinoki et al. |
| 2009/0129679 | A1 | * | 5/2009 | Miyamoto ...................... 382/190 |
| 2009/0285461 | A1 | * | 11/2009 | Bohm et al. .................. 382/128 |
| 2012/0250974 | A1 | * | 10/2012 | Miyamoto ...................... 382/132 |

FOREIGN PATENT DOCUMENTS

| JP | 62-247232 | 10/1987 |
| JP | 2003-159210 | 6/2003 |
| JP | 2005-021580 | 1/2005 |
| JP | 2005-204958 | 8/2005 |
| JP | 2007-209219 | 8/2007 |
| JP | 2009-226065 | 10/2009 |

OTHER PUBLICATIONS

International Search Report dated May 10, 2011 issued in PCT/JP2011/053206.

* cited by examiner

Primary Examiner — Stephen R Koziol
Assistant Examiner — Sean Conner
(74) Attorney, Agent, or Firm — Scully, Scott, Murphy & Presser, P.C.

(57) ABSTRACT

A fluoroscopy apparatus includes a light-source device that generates illumination light and excitation light; a fluorescence-image generating unit that generates a fluorescence image based on irradiation with the excitation light; a white-light-image generating unit that generates a white-light image based on irradiation with the illumination light; a fluorescence-image correcting unit that generates a corrected fluorescence image by dividing the signal strengths of pixels in the fluorescence image by the signal strengths of pixels in the white-light image; a characteristic-value acquiring unit that extracts the characteristic value of the corrected fluorescence image; a threshold setting unit that sets a threshold for determining a region of interest in the corrected fluorescence image using a history of characteristic values extracted by the characteristic-value acquiring unit; and a pseudo-color-image generating unit that discriminates between a region of interest and another region in the corrected fluorescence image on the basis of the threshold.

14 Claims, 11 Drawing Sheets

FLUOROSCOPY APPARATUS

CROSS-REFERENCE TO RELATED APPLICATIONS

This is a continuation of International Application PCT/JP2011/053206, with an international filing date of Feb. 16, 2011, which is hereby incorporated by reference herein in its entirety. This application is based on Japanese Patent Application No. 2010-067019, the contents of which are incorporated herein by reference.

TECHNICAL FIELD

The present invention relates to a fluoroscopy apparatus.

BACKGROUND ART

Since the intensity of irradiated light changes depending on the examination distance in conventional fluoroscopy apparatuses for diagnosing affected regions using fluorescent agents, there is a known method of correcting fluorescence images by dividing a fluorescence-image signal strength by a reference-light-image signal strength (for example, refer to PTL 1).

For an endoscopic apparatus designed to examine autofluorescence, there is a known method of displaying a fluorescence image containing only pixels whose ratio of a fluorescence-image signal strength to a reference-light-image signal strength is larger than or equal to a predetermined threshold such that the position of an affected region is easily located (for example, refer to PTL 2).

CITATION LIST

Patent Literature

{PTL 1}
Japanese Unexamined Patent Application, Publication No. SHO-62-247232
{PTL 2}
Japanese Unexamined Patent Application, Publication No. 2005-21580

SUMMARY OF INVENTION

The present invention employs a fluoroscopy apparatus including a light source unit configured to generate illumination light and excitation light to be radiated onto an imaging subject; a fluorescence-image generating unit configured to generate a fluorescence image by imaging fluorescence generated at the imaging subject as a result of being irradiated with the excitation light emitted from the light source unit; a return-light-image generating unit configured to image returning light from the imaging subject irradiated with illumination light from the light source unit and generate a return-light image; an image correcting unit configured to generate a corrected fluorescence image by dividing the signal strengths of pixels in the fluorescence image generated by the fluorescence-image generating unit by signal strengths of pixels in the return-light image generated by the return-light-image generating unit; a characteristic-value extracting unit configured to extract a characteristic value of the corrected fluorescence image generated by the image correcting unit; a threshold determining unit configured to determine a threshold for discrimination between a region of interest and another region of the corrected fluorescence image using a history of characteristic values extracted by the characteristic-value extracting unit; and a discriminating unit configured to discriminate between the region of interest and another region in the corrected fluorescence image on the basis of the threshold determined by the threshold determining unit.

BRIEF DESCRIPTION OF DRAWINGS

FIG. 1 is a functional block diagram of a fluoroscopy apparatus according to a first embodiment of the present invention.
FIG. 2 is a graph showing the transmittance characteristics of an excitation-light transmitting filter in FIG. 1.
FIG. 3 is a graph showing the transmittance characteristics of an excitation-light cut filter in FIG. 1.
FIG. 4 is a histogram of the signal strengths of pixels in a corrected fluorescence image, where a region of interest is not included in the image.
FIG. 5 is a histogram of the signal strengths of the pixels in the corrected fluorescence image, where a region of interest is included in the image.
FIG. 6 is a graph showing time variation of a characteristic value.
FIG. 7 illustrates a method of setting a threshold, where
FIG. 7(a) illustrates a case of selection based on set numbers,
FIG. 7(b) illustrates a case of selection using a toggle,
FIG. 7(c) shows a case of direct input,
and FIG. 7(d) shows a case of selection based on automatically divided numbers.
FIG. 8 is a functional block diagram of a fluoroscopy apparatus according to a second embodiment of the present invention.
FIG. 9 illustrates a histogram of the signal strengths of characteristic values when a region of interest is not included, where
FIG. 9(a) illustrates time variation,
and FIG. 9(b) is a histogram.
FIG. 10 is a graph showing a histogram of the signal strengths of characteristic values when a region of interest is included, where
FIG. 10(a) illustrates time variation,
and FIG. 10(b) is a histogram.
FIG. 11 is a flow chart illustrating a method of automatically setting a threshold.
FIG. 12 is a functional block diagram of a fluoroscopy apparatus according to a first modification.
FIG. 13 is a functional block diagram illustrating a fluoroscopy apparatus according to a second modification.

DESCRIPTION OF EMBODIMENTS

First Embodiment
A fluoroscopy apparatus 1 according to a first embodiment of the present invention will now be described with reference to the drawings. Here, an example in which the fluoroscopy apparatus 1 according to this embodiment is applied to an endoscopic apparatus will be described.

Figure 1:
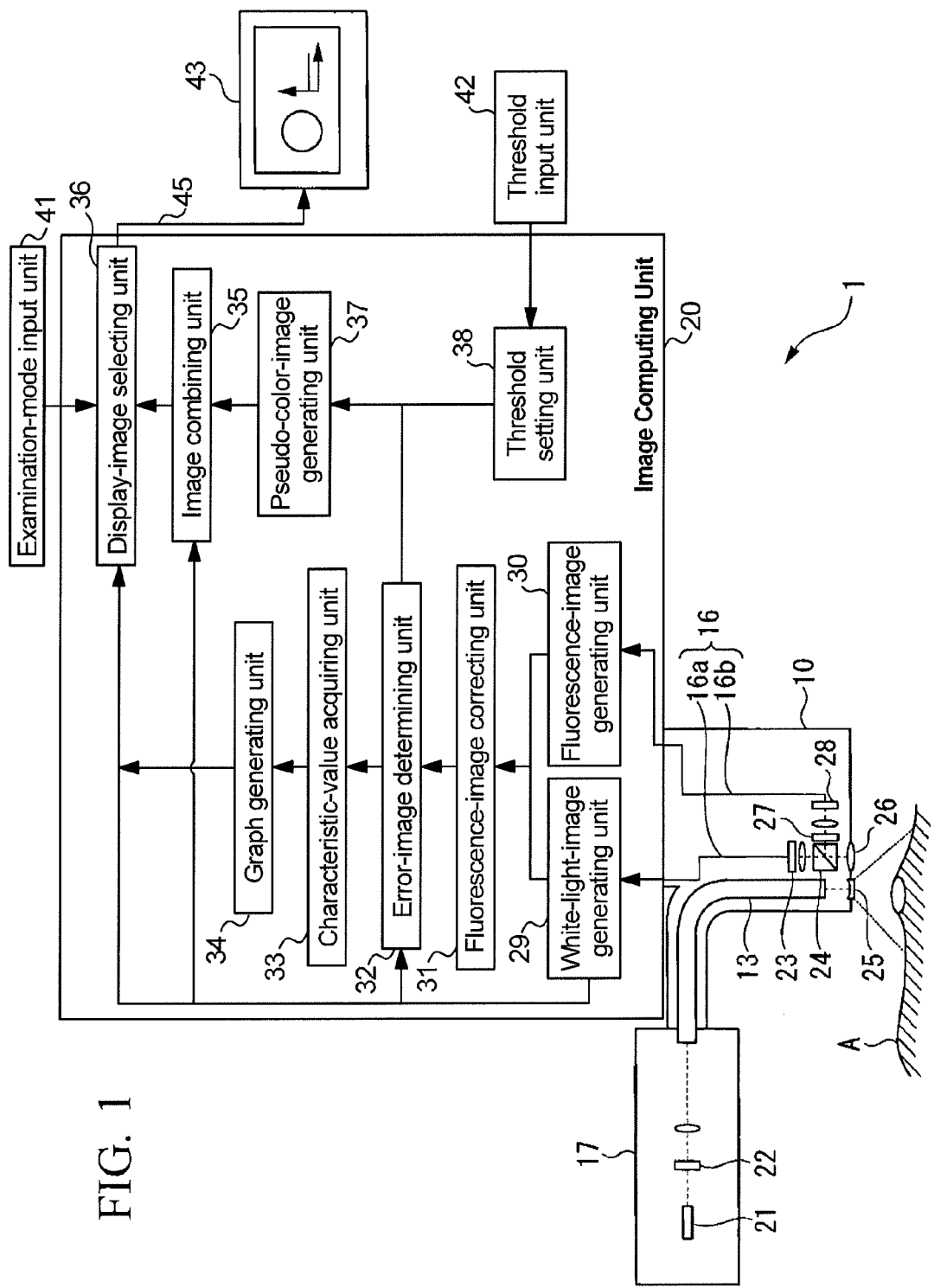
{FIG. 1}

As illustrated in FIG. 1, the fluoroscopy apparatus 1 includes an endoscope 10, a light source device (light source unit) 17, an image computing unit 20, and a monitor (characteristic-value display unit) 43.

The endoscope 10 has a long, thin insertion part that is to be inserted into a body cavity, and a light-guide fiber 13 is disposed inside the endoscope 10. One end of the light-guide fiber 13 extends to the tip of the endoscope 10, and the other end thereof is connected to the light-source device 17. In this way, light emitted from the light-source device 17 is guided to the tip of the endoscope 10 and is incident on a subject A (imaging subject) inside the body cavity.

The endoscope 10 and the image computing unit 20 are connected via image transmission cables 16. The image computing unit 20 and the monitor 43 are connected via a monitor cable 45. In this way, the image data acquired by the endoscope 10 is transmitted through the image transmission cables 16 to the image computing unit 20. The sent image data is subjected to image-processing in the image computing unit 20, is transmitted to the monitor 43 through the monitor cable 45, and is displayed on the monitor screen.

The image computing unit 20 is connected to an examination-mode input unit 41 and a threshold input unit (signal-strength input unit) 42. Information input to the examination-mode input unit 41 and the threshold input unit 42 is sent to the image computing unit 20, and the image data received from the endoscope 10 is processed in the image computing unit 20.

Next, a detailed configuration of the fluoroscopy apparatus 1 according to this embodiment and the monitor screen display will be described.

Figure 2:
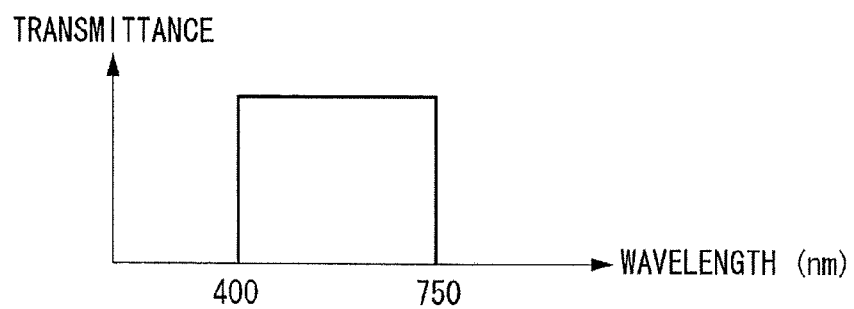
{FIG. 2}

As illustrated in FIG. 1, a xenon lamp (Xe lamp) 21 and a wavelength selection filter 22 are disposed inside the light-source device 17. The xenon lamp 21 generates white light and excitation light. The light generated at the xenon lamp 21 is passed through the wavelength selection filter 22, through which only white light and excitation light in a predetermined wavelength band pass. Specifically, as illustrated in FIG. 2, the wavelength selection filter 22 transmits light in a wavelength band of 400 to 750 nm and reflects light in other wavelength bands.

As illustrated in FIG. 1, the endoscope 10 accommodates the light-guide fiber 13, a white-light color CCD 23, a splitter 24, an illumination optical system 25, an image-acquisition optical system 26, an excitation-light cut filter 27, and a fluorescence monochrome CCD 28.

The white light and the excitation light emitted from the light-source device 17 is guided through the light-guide fiber 13 in the endoscope 10 and is made incident on the subject A from the illumination optical system 25 disposed at the tip of the endoscope 10. As a result of the subject A being irradiated with white light, the light reflected at the subject A enters the image-acquisition optical system 26 disposed at the tip of the endoscope 10. As a result of the subject A being irradiated with the excitation light, fluorescence is generated in the subject A, and the fluorescence enters the image-acquisition optical system 26.

The splitter 24 transmits the light reflected at the subject A while reflecting the fluorescence generated in the subject A. By possessing such characteristics, the splitter 24 separates the reflected light and the fluorescence that have entered the image-acquisition optical system 26. Since the wavelength of the fluorescence at this time is shifted further toward the long wavelength side than the wavelength of the excitation light, a splitter that reflects light further toward the long wavelength side than the wavelength of the excitation light is used.

Figure 3:
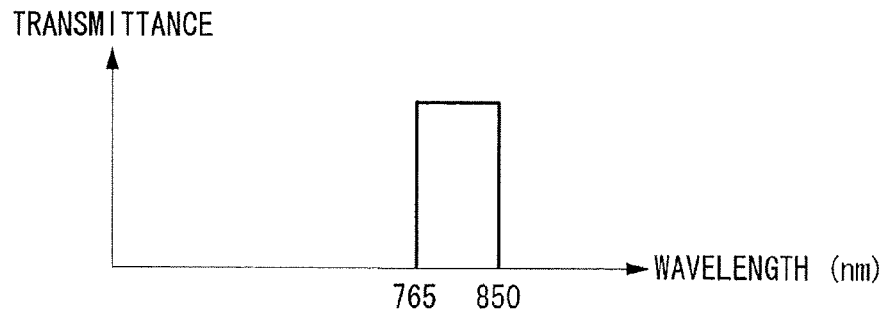
{FIG. 3}

The excitation-light cut filter 27 is a filter for removing excitation light (reflected light) from the fluorescence. Specifically, as illustrated in FIG. 3, the splitter 24 transmits light in the wavelength band of 765 to 850 nm and reflects light in other wavelength bands.

By passing through the excitation-light cut filter 27, the fluorescence is completely separated from the excitation light (reflected light), and the separated fluorescence is detected by the fluorescence monochrome CCD 28. Since the separated fluorescence is weak, the sensitivity of the fluorescence monochrome CCD 28 used is higher than that of the white-light color CCD 23. The fluorescence image data detected by the fluorescence monochrome CCD 28 is sent to a fluorescence-image generating unit 30 in the image computing unit 20 via an image transmission cable 16b.

Meanwhile, the light reflected at the subject A and transmitted through the splitter 24 is detected by the white-light color CCD 23. The white-light image data detected by the white-light color CCD 23 is sent to a white-light-image generating unit (return-light-image generating unit) 29 in the image computing unit 20 via an image transmission cable 16a.

As illustrated in FIG. 1, the image computing unit 20 has the functions of the white-light-image generating unit 29, the fluorescence-image generating unit 30, a fluorescence-image correcting unit (image correcting unit) 31, an error-image determining unit (error determining unit) 32, a characteristic-value acquiring unit 33, a graph generating unit (characteristic-value recording unit) 34, an image combining unit 35, a display-image selecting unit 36, a pseudo-color-image generating unit (discriminating unit) 37, and a threshold setting unit (threshold determining unit) 38. The examination-mode input unit 41 is connected to the display-image selecting unit 36, and the threshold input unit 42 is connected to the threshold setting unit 38.

The white-light-image generating unit 29 generates a white-light image from the white-light image data detected by the white-light color CCD 23. The white-light-image generating unit 29 sends the generated white-light image to the error-image determining unit 32, the image combining unit 35, and the display-image selecting unit 36.

The fluorescence-image generating unit 30 generates a fluorescence image from the fluorescence image data detected by the fluorescence monochrome CCD 28. The fluorescence-image generating unit 30 sends the generated fluorescence image to the fluorescence-image correcting unit 31.

The fluorescence-image correcting unit 31 generates a corrected fluorescence image by dividing the luminance values of the pixels in the fluorescence image generated by the fluorescence-image generating unit 30 by the luminance values of the pixels in the white-light image generated by the white-light-image generating unit 29 corresponding to pixels in the fluorescence image. The fluorescence-image correcting unit 31 transmits the generated corrected fluorescence image to the error-image determining unit 32.

The error-image determining unit 32 detects the signal strengths of the pixels in the white-light image acquired by the white-light-image generating unit 29 and performs error determination if the number of pixels having a saturated signal strength is larger than a predetermined number of pixels. Furthermore, in a case in which the error-image determining unit 32 performs error determination, the corrected fluorescence image generated by the fluorescence-image correcting unit 31 is not sent to the characteristic-value acquiring unit 33 or the pseudo-color-image generating unit 37.

Figure 4:
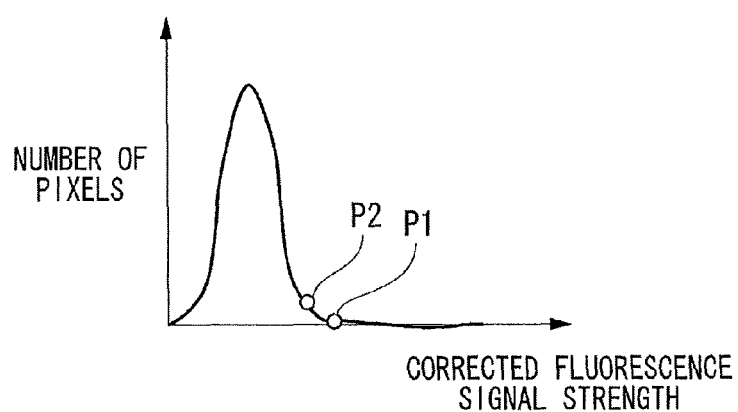
{FIG. 4}

The characteristic-value acquiring unit 33 extracts a characteristic value of the corrected fluorescence image generated by the fluorescence-image correcting unit 31. Specifically, as illustrated in FIG. 4, the characteristic-value acquiring unit 33 generates a histogram of the signal strengths of the pixels in the corrected fluorescence image and extracts the maximum value (point P1 in FIG. 4) of the signal strengths of the corrected fluorescence image in the histogram as a characteristic value.

In this way, a characteristic value can be easily extracted from a corrected fluorescence image, allowing the processing performed by the characteristic-value acquiring unit 33 to be simplified.

The characteristic-value acquiring unit 33 may extract, from the histogram of the signal strengths of the pixels in the corrected fluorescence image, the signal strength corresponding to a predetermined cumulative value of the signal strengths of the pixels in the corrected fluorescence image (point P2 in FIG. 4) as the characteristic value.

In this way, the characteristic value extracted from the corrected fluorescence image can be changed in response to the image conditions, etc. For example, by extracting the signal strength corresponding to a cumulative value of the signal strengths of the pixels in the corrected fluorescence image equaling 98% as a threshold, a threshold for discrimination between a region of interest corresponding to signal strengths larger than the characteristic value and another region can be set while precluding abnormal values due to noise, etc.

Figure 5:
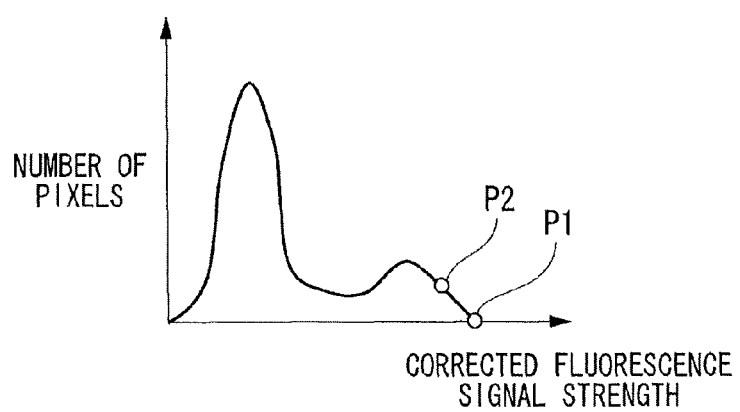
{FIG. 5}

Now, if the subject A being examined does not have a region of interest, the histogram of the corrected fluorescence image has only one large peak that appears where the signal strength is small, as illustrated in FIG. 4. Alternatively, if a region of interest is included in the examination visual field, as illustrated in FIG. 5, a new peak in addition to the peak where the signal strength is small appears because a region with large signal strengths exists in the fluorescence image.

The graph generating unit 34 has an internal memory, which is not shown in the drawing (drawing omitted), associates the signal strengths of the characteristic values extracted by the characteristic-value acquiring unit 33 and the detection time thereof, and stores them in the memory. In this way, as illustrated in FIG. 6, the graph generating unit 34 generates a graph of the time variation of the characteristic values extracted by the characteristic-value acquiring unit 33 and sends this graph to the display-image selecting unit 36 as an image to be displayed on the monitor 43.

Figure 6:
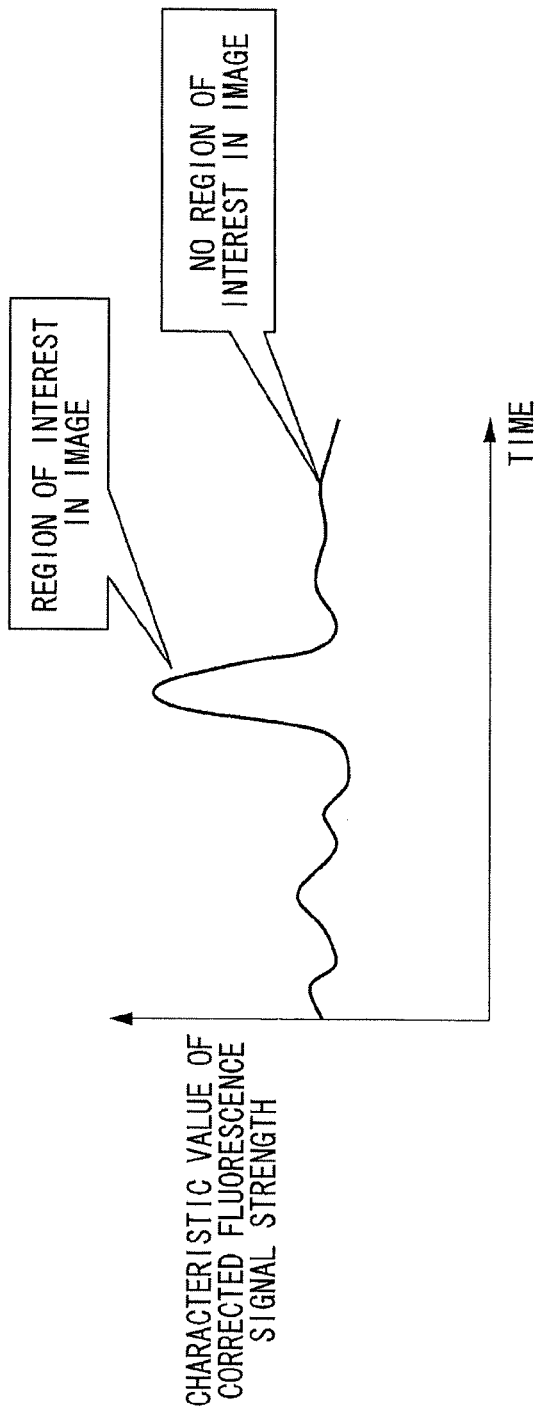
{FIG. 6}

In the graph of the time variation of the characteristic values shown in FIG. 6, if a region of interest does not exist in the examination region, the values in the graph are substantially constant. Alternatively, if a region of interest exists in the examination region, a peak appears in the graph because a region having large signal strengths exists in the corrected fluorescence image.

The threshold input unit 42 allows a user to input a signal strength (threshold) that is to be set as a reference for region-of-interest discrimination in the graph of the time variation of the characteristic values prepared by the graph generating unit 34 and displayed on the monitor 43. Specifically, as illustrated in FIG. 7(a), the threshold input unit 42 displays the signal strengths (vertical axis) of the characteristic values by discrete numbers in the graph of the time variation of the characteristic values to allow a user to select one of the numbers as an input for the signal strength that is to be set as a reference for region-of-interest discrimination.

Figure 7:
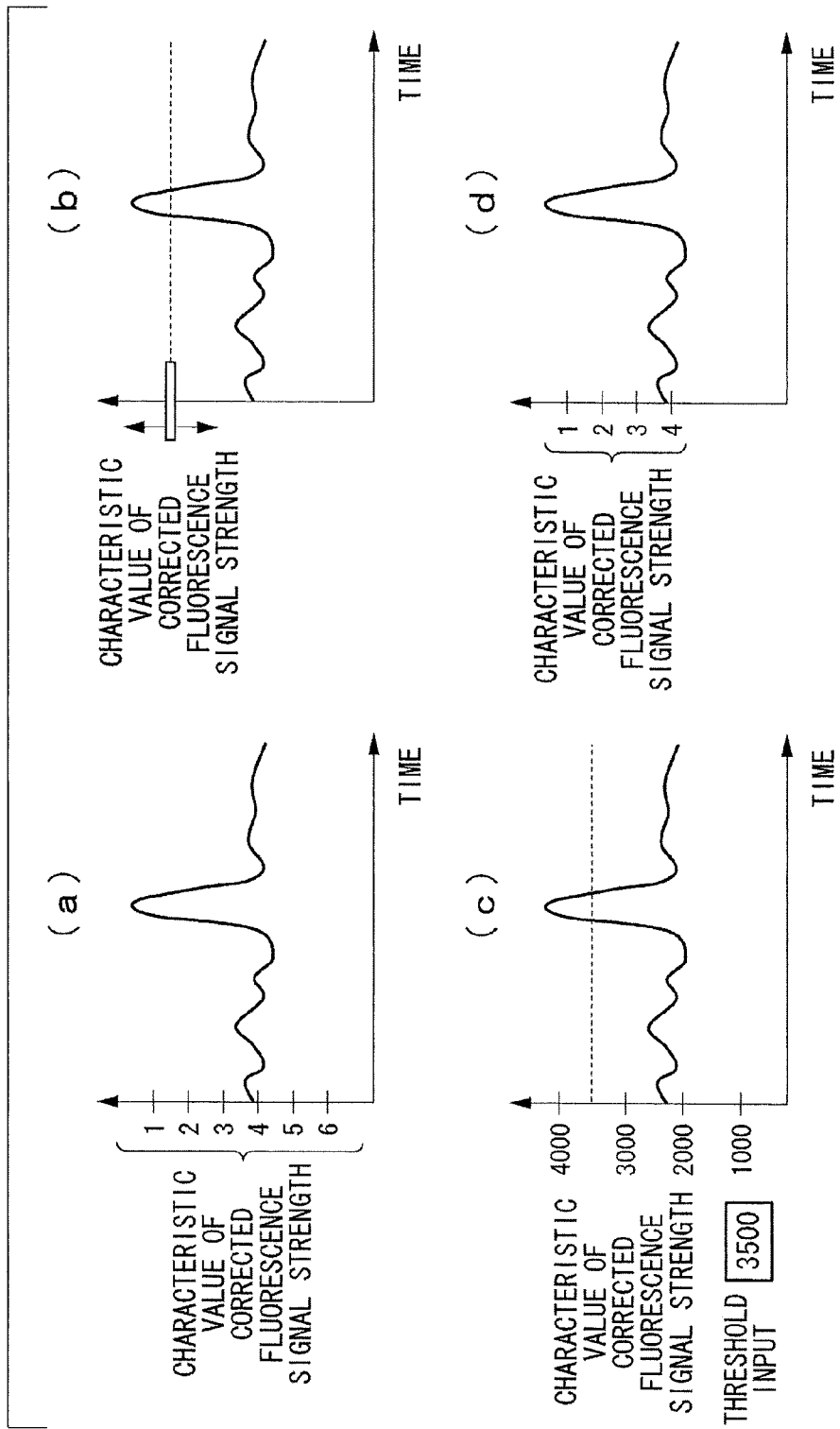
{FIG. 7}

As illustrated in FIG. 7(b), the threshold input unit 42 may allow a user to use a mouse, etc. to input the signal strength that is to be set as a reference for region-of-interest discrimination by vertically moving a toggle displayed on the vertical axis of the graph of the time variation of the characteristic values.

As illustrated in FIG. 7(c), the threshold input unit 42 may allow a user to use a keyboard, etc. to directly input the signal strength (threshold) that is to be set as a reference for region-of-interest discrimination in the graph of the time variation of the characteristic values.

As illustrated in FIG. 7(d), the threshold input unit 42 may display numbers preset by automatically dividing the interval between the maximum value and minimum value of the signal strengths into steps in the graph of the time variation of the characteristic values and may allow a user to select one of these numbers to input the signal strength to be set as a reference for region-of-interest discrimination.

The threshold setting unit 38 sets the signal strength input to the threshold input unit 42 as a threshold for discrimination between a region of interest and another region and sends the threshold to the pseudo-color-image generating unit 37.

The pseudo-color-image generating unit 37 assigns colors to the pixels (pseudo-colorization) in the corrected fluorescence image sent from the error-image determining unit 32 based on the difference between the signal strengths of the pixels and the threshold determined by the threshold setting unit 38. Specifically, pixels that have signal strengths larger than the threshold determined by the threshold setting unit 38 are assigned red, green, and blue, in this order, starting from pixels with higher signal strengths. Zero (black) is assigned to pixels having signal strengths smaller than or equal to the threshold determined by the threshold setting unit 38.

The image combining unit 35 combines the white-light image generated by the white-light-image generating unit 29 and the corrected fluorescence image pseudo-colorized by the pseudo-color-image generating unit 37 to generate a combined image. Specifically, the image combining unit 35 generates a combined image by selecting pixels of the white-light image for pixels that are assigned zero (black) in the pseudo-colorized corrected fluorescence image and selecting pixels of the pseudo-colorized corrected fluorescence image for pixels that are assigned values other than zero.

The examination-mode input unit 41 allows a user to set the examination mode for displaying an image on the monitor 43 from a plurality of examination modes. Here, the examination modes include, for example, an examination mode in which a white-light image generated by the white-light-image generating unit 29 is directly displayed on the monitor 43 (white-light-image examination mode), an examination mode in which a combined image generated by the image combining unit 35 is displayed on the monitor 43 (combined-image examination mode), and an examination mode in which a white-light image and a combined image are simultaneously displayed (two-image examination mode).

The display-image selecting unit 36 selects the white-light image and/or the combined image based on the examination mode set by the examination-mode input unit 41 and displays the selected image on the monitor 43. The display-image selecting unit 36 displays the graph of the time variation of the characteristic values generated by the graph generating unit 34 on the monitor 43.

The monitor 43 displays the image selected by the display-image selecting unit 36 and the graph of the time variation of the characteristic values generated by the graph generating unit 34.

The operation of the fluoroscopy apparatus 1 having the above-described configuration will now be described.

Upon starting examination of the subject A using the fluoroscopy apparatus 1 according to this embodiment, the subject A is irradiated with light from the light-source device 17 via the light-guide fiber 13. In this way, a white-light image generated from light reflected at the subject A is acquired by the white-light-image generating unit 29, while a fluorescence image generated from fluorescence emitted from the subject A is acquired by the fluorescence-image generating unit 30.

Next, the fluorescence-image correcting unit 31 generates a corrected fluorescence image by dividing the luminance values of pixels in the fluorescence image by the luminance values of pixels in the white-light image, and then error determination is performed by the error-image determining unit 32. When error determination is performed, the white-light image is directly displayed on the monitor 43.

Alternatively, when error determination is not performed, characteristic values of the corrected fluorescence image are extracted by the characteristic-value acquiring unit 33, and then a graph of the time variation of the characteristic values is generated by the graph generating unit 34. The generated graph of the time variation of the characteristic values is displayed on the monitor 43 and is used for setting the signal strength that is to be set as a reference for region-of-interest discrimination.

The user inputs the signal strength that is to be set as a reference for region-of-interest discrimination to the threshold input unit 42, and this signal strength is set as the threshold for discrimination between normal tissue and affected tissue.

The pseudo-color-image generating unit 37 pseudo-colorizes the corrected fluorescence image on the basis of the preset color assignment and the threshold set by the threshold setting unit 38.

The pseudo-colorized corrected fluorescence image is combined with the white-light image by the image combining unit 35. The combined image generated in this way is displayed on the monitor 43 in accordance with the examination mode set on the examination-mode input unit 41.

As described above, with the fluoroscopy apparatus 1 according to this embodiment, a fluorescence image containing only pixels having a ratio of the signal strength of the fluorescence image to the signal strength of the white-light image higher than or equal to a predetermined threshold can be displayed so that the position of a region of interest on the subject A can be easily located.

The ability to metabolize fluorescent agents varies among individuals, and each patient and each site have different tissue color. Thus, for each imaging subject, the ratio of the signal strength of the fluorescence image to the signal strength of the white-light image in a region of interest differs from the ratio of the signal strength of the fluorescence image to the signal strength of the white-light image in another region.

To address this, the fluoroscopy apparatus 1 according to this embodiment determines a threshold for discrimination between a normal region and an affected region on the basis of the characteristic value of the corrected fluorescence image obtained by dividing the fluorescence image by the white-light image; therefore the threshold can be changed in accordance with each patient. Hence, discrimination between a region of interest and another region can be performed in accordance with each imaging subject. Accordingly, the examination accuracy of an affected region can be improved.

Since the threshold setting unit 38 sets the signal strength input to the threshold input unit 42 as the threshold, the threshold for discrimination between a region of interest and another region can be arbitrarily determined by the user inputting the signal strength to the threshold input unit 42 while observing the time variation of the characteristic values displayed on the monitor 43.

When the tip of the endoscope 10 contacts the tissue wall, most of the pixels in the white-light image are saturated, and thus the corrected fluorescence image will have an abnormally low value. Thus, the user can recognize an abnormal state by performing error determination with the error-image determining unit 32 when the number of pixels whose signal strength is saturated in the white-light image is larger than a predetermined number of pixels.

The error-image determining unit 32 may detect the signal strengths of the pixels in the corrected fluorescence image generated by the fluorescence-image correcting unit 31 and perform error determination when the number of pixels whose signal strength is saturated is larger than a predetermined number of pixels.

Since the exposure time differs between a white-light image and a fluorescence image when the endoscope is moved quickly, the images do not match because some pixels that are contained in the fluorescence image will not be contained in the white-light image. In such a case, the corrected fluorescence image is divided by zero, causing abnormally bright spots. Thus, the user can recognize an abnormal state by performing error determination with the error-image determining unit 32 when the number of pixels whose signal strength is saturated in the corrected fluorescence image is larger than a predetermined number of pixels.

Furthermore, when the error-image determining unit 32 performs error determination, characteristic value extraction by the characteristic-value acquiring unit 33 and pseudo-colorization by the pseudo-color-image generating unit 37 are interrupted, and the white-light image is directly displayed on the monitor 43; in this way, examination in an abnormal state can be prevented, and examination accuracy can be improved.

Second Embodiment

Next, a fluoroscopy apparatus 2 according to a second embodiment of the present invention will now be described with reference to the drawings. In the description of this embodiment, a description of commonalities with the fluoroscopy apparatus 1 according to the first embodiment is omitted, and differences will mainly be described.

The fluoroscopy apparatus 2 according to this embodiment differs from the fluoroscopy apparatus 1 according to the first embodiment in that the threshold for discrimination between a normal region and an affected region is set automatically.

Figure 8:
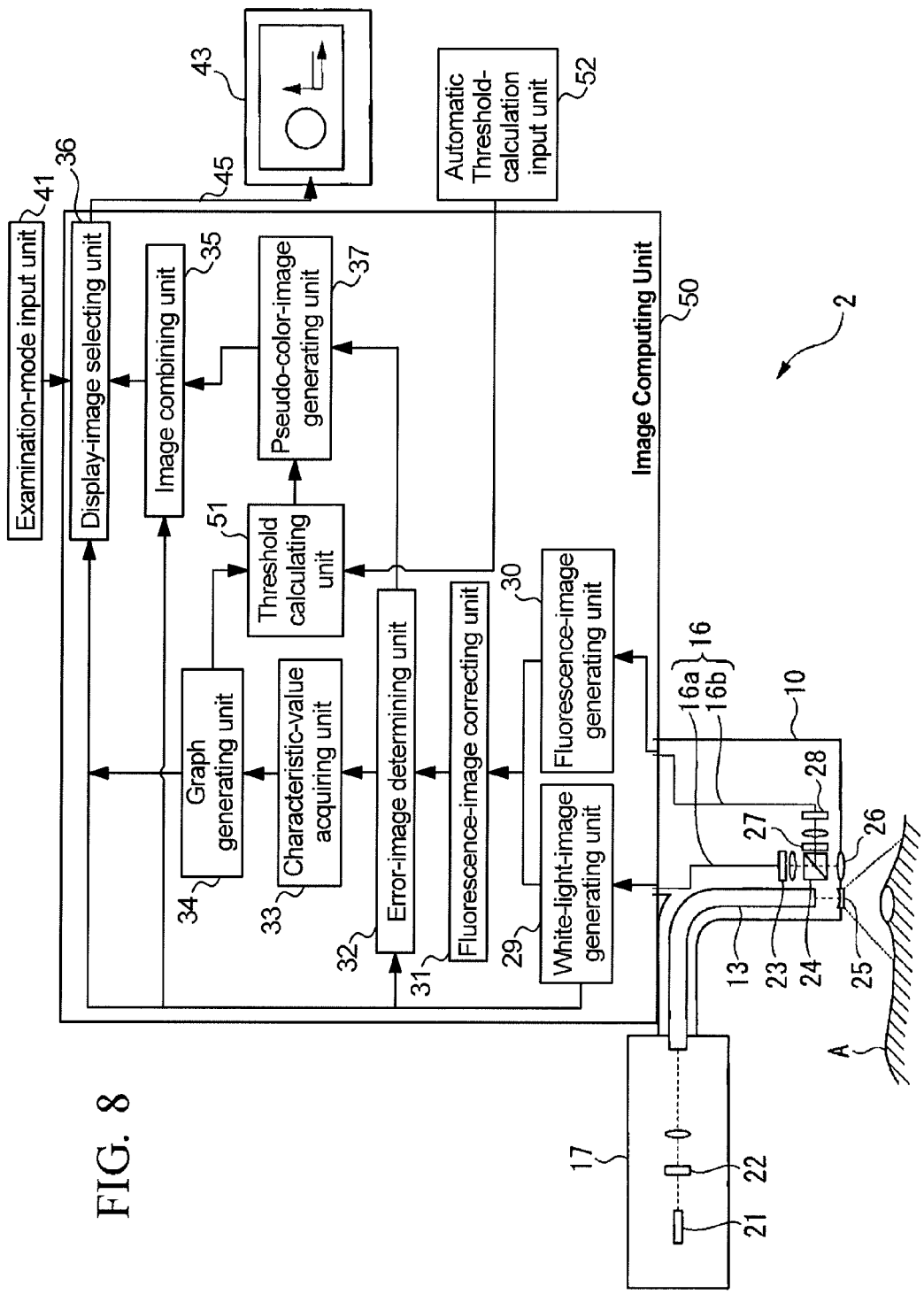
{FIG. 8}

As illustrated in FIG. 8, an image computing unit 50 of the fluoroscopy apparatus 2 according to this embodiment includes a threshold calculating unit (threshold determining unit) 51 and is connected to an automatic threshold-calculation input unit (threshold setting instruction unit) 52.

The automatic threshold-calculation input unit 52 instructs the timing for setting the threshold for discrimination between a normal region and an affected region.

Upon input of an instruction from the automatic threshold-calculation input unit 52, the threshold calculating unit 51 reads out the time variation of the characteristic values recorded in the graph generating unit 34 and calculates a threshold for discrimination between a region of interest and another region.

Figure 9:
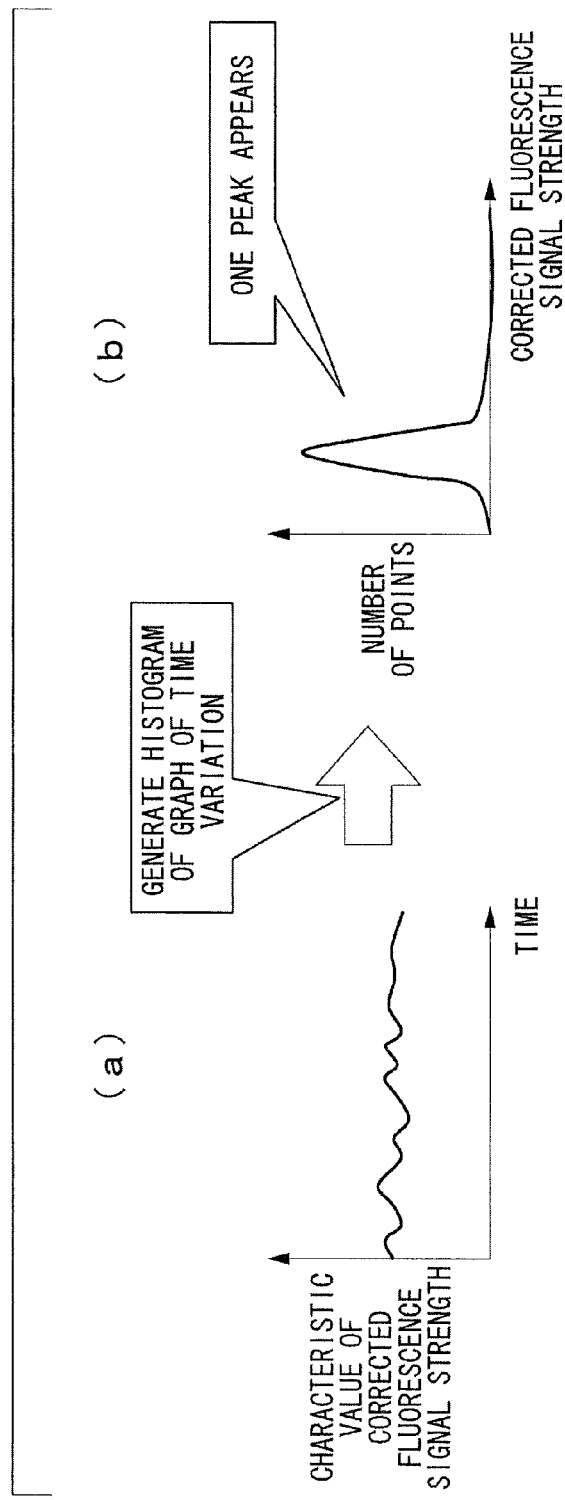
{FIG. 9}
Figure 10:
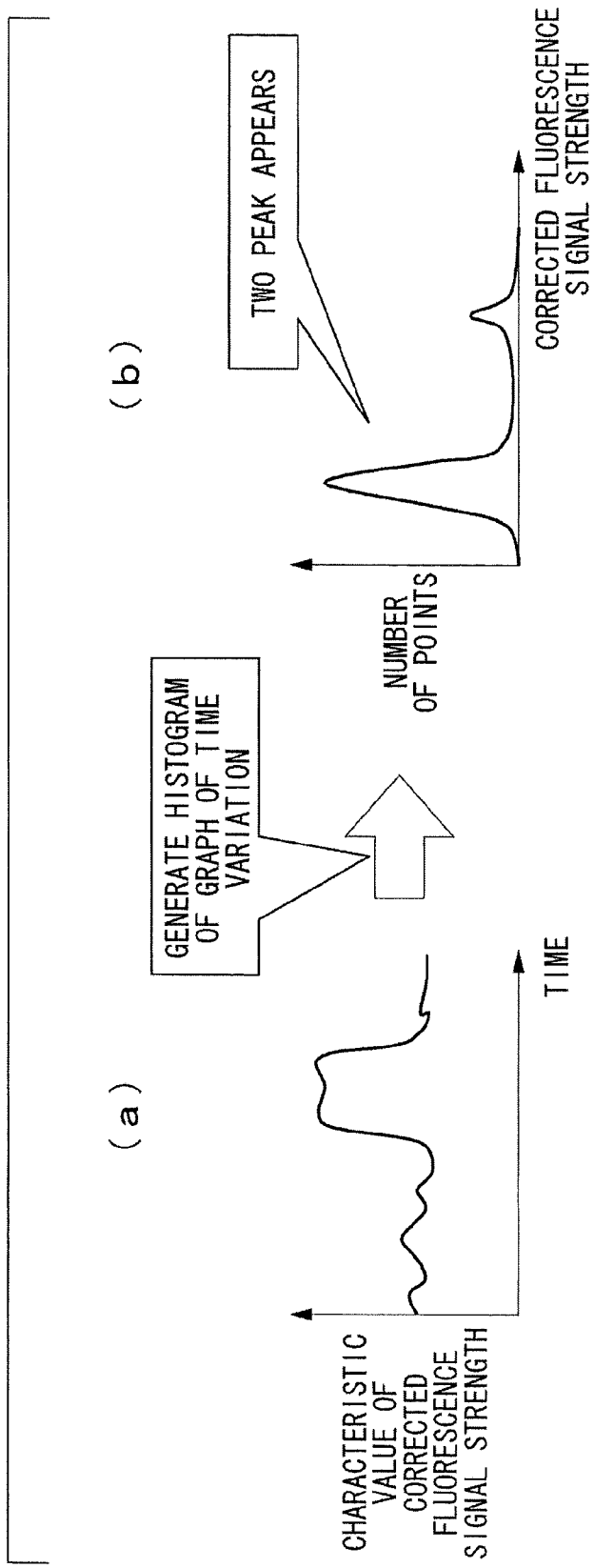
{FIG. 10}

Specifically, the threshold calculating unit 51 generates a histogram of the signal strengths of the characteristic values over time, such as those illustrated in FIGS. 9(b) and 10(b), from the time variation of the characteristic values recorded in the graph generating unit 34, as illustrated in FIGS. 9(a) and 10(a). Then, the threshold calculating unit 51 detects the number of peaks in the histograms illustrated in FIGS. 9(b) and 10(b) and sets the peak signal strength as a threshold value.

That is, as shown in FIG. 9(a), if the signal strength in the graph of the time variation of the characteristic values is substantially constant, this indicates that a region of interest does not exist in the examination region. In such a case, as shown in FIG. 9(b), only one peak appears in the histogram of the signal strengths of the characteristic values over time. In such a case, the threshold calculating unit 51 sets the signal strength at the peak as the threshold.

Meanwhile, as shown in FIG. 10(a), a large fluctuation in the signal strength in the graph of the time variation of the characteristic values indicates that a region of interest is included in the examination region. In such a case, as shown in FIG. 10(b), multiple peaks appear in the histogram of the signal strengths of the characteristic values over time. In such a case, the threshold calculating unit 51 sets the signal strength at a value between the largest signal strength peak and the smallest signal strength peak, among the peaks.

The threshold determined in such a manner is transmitted to the pseudo-color-image generating unit 37 and is used for pseudo-colorization of the corrected fluorescence image transmitted from the error-image determining unit 32. Specifically, colors (for example, red, green, and blue) are assigned to the pixels having signal strengths larger than the threshold determined by the threshold calculating unit 51, and zero (black) is assigned to the pixels having signal strengths smaller than or equal to the threshold determined by the threshold setting unit 38.

The operation of the fluoroscopy apparatus 2 having the above-described configuration will now be described.

Upon starting examination of the subject A using the fluoroscopy apparatus 2 according to this embodiment, the subject A is irradiated with light from the light-source device 17 via the light-guide fiber 13. In this way, a white-light image generated from light reflected at the subject A is acquired by the white-light-image generating unit 29, while a fluorescence image generated from fluorescence emitted from the subject A is acquired by the fluorescence-image generating unit 30.

Next, the fluorescence-image correcting unit 31 generates a corrected fluorescence image by dividing the signal strengths of pixels in the fluorescence image by the signal strengths of pixels in the white-light image, and then error determination is performed by the error-image determining unit 32. When error determination is performed, the white-light image is directly displayed on the monitor 43.

Alternatively, when error determination is not performed, the characteristic value of the corrected fluorescence image is extracted by the characteristic-value acquiring unit 33, and then a graph of the time variation of the characteristic values is generated by the graph generating unit 34. The generated graph of the time variation of the characteristic values is displayed on the monitor 43. In this embodiment, as described below, the threshold for discrimination between a region of interest and another region is automatically set; thus, the graph of the time variation of the characteristic values does not necessarily have to be displayed.

Figure 11:
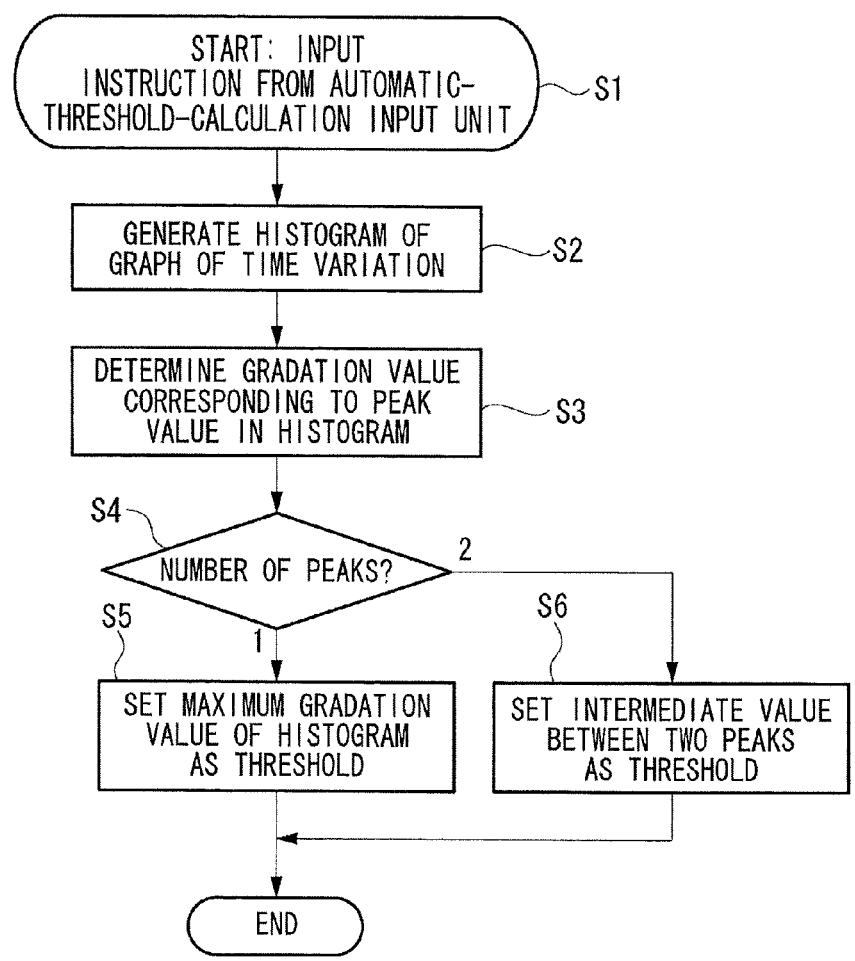
{FIG. 11}

The method of setting the threshold performed by the threshold calculating unit 51 will now be described below with reference to the flow chart in FIG. 11.

Upon receiving an instruction from the user for setting a threshold from the automatic threshold-calculation input unit 52 (Step S1), as illustrated in FIGS. 9(b) and 10(b), a histogram of the signal strengths of the characteristic values over time is generated by the threshold calculating unit 51 from the time variation of the characteristic values recorded in the graph generating unit 34 (Step S2).

Next, the threshold calculating unit 51 determines the gradation values (signal strengths) of the peak values in the histogram generated as described above (Step S3), and the number of peaks is determined (Step S4).

In Step S4, if the number of peaks is one, the maximum signal strength (gradation value) thereof is set as the threshold (Step S5). If the number of peaks is two, a signal strength between these peaks (for example, an intermediate value) is set as the threshold (Step S6).

The corrected fluorescence image is pseudo-colorized by the pseudo-color-image generating unit 37 on the basis of the threshold set by the threshold calculating unit 51 in such a manner as described above and the preset color assignment.

The pseudo-colorized corrected fluorescence image is combined with the white-light image by the image combining unit 35. The combined image generated in such a manner is displayed on the monitor 43 in accordance with the examination mode set using the examination-mode input unit 41.

As described above, the fluoroscopy apparatus 2 according to this embodiment can set a threshold for discrimination between a region of interest and another region at a timing input to the automatic threshold-calculation input unit 52 by the user. By reading out the time variation of the characteristic values recorded in the graph generating unit 34 and generating a histogram of the signal strengths of the characteristic values over time, the threshold calculating unit 51 can set a threshold for automatic discrimination between a region of interest and another region.

If the number of peaks in this histogram is one, it can be determined that only a region not including a region of interest is examined; thus, the maximum signal strength can be set as the threshold for discrimination between a region of interest and another region. If the number of peaks in the histogram is two or more, it can be determined that a region of interest and another region are both examined; thus, a signal strength at a value between the largest signal strength peak and the smallest signal strength peak, among the peaks, can be set as the threshold for discrimination between a normal region and an affected region. Then, it is possible to perform discrimination between a region of interest and another region, appropriate for the imaging subject. In this way, the examination accuracy of an affected region can be improved.

First Modification

Next, a first modification of the fluoroscopy apparatus 2 according to the second embodiment will be described.

A fluoroscopy apparatus 3 according to this modification differs from the fluoroscopy apparatus 2 according to the second embodiment in that the timing for setting a threshold for discrimination between a region of interest and another region is determined on the basis of the number of data items recorded in the graph generating unit 34.

Figure 12:
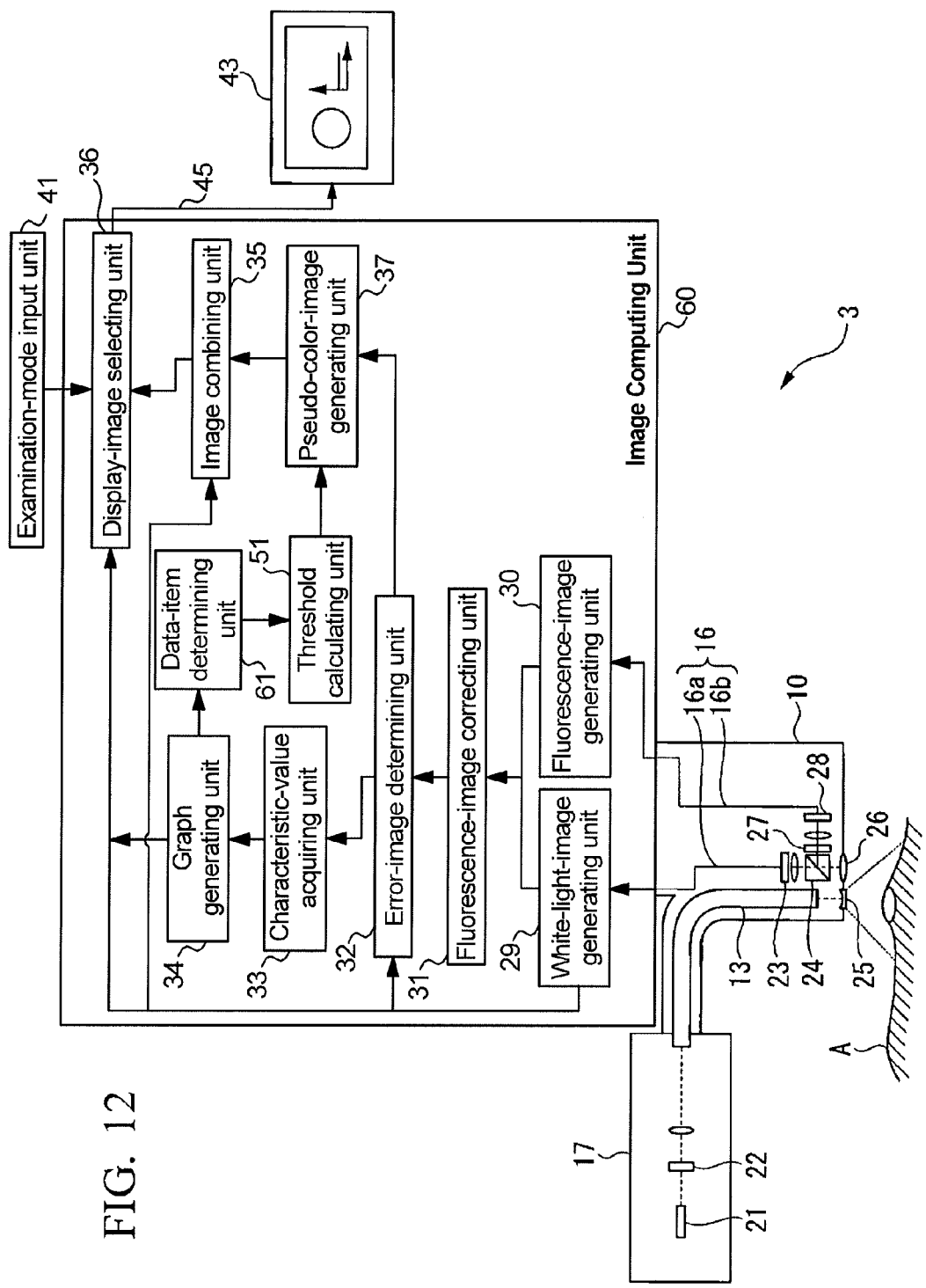
{FIG. 12}

As illustrated in FIG. 12, an image computing unit 60 of the fluoroscopy apparatus 3 according to this modification includes a data-item determining unit 61.

The data-item determining unit 61 counts the number of characteristic-value data items, recorded in the graph generating unit 34, for the corrected fluorescence image and, when the number of data items equals a predetermined value, instructs the threshold calculating unit 51 about the timing for setting the threshold for discrimination between a region of interest and another region.

In this way, the threshold value for discrimination between a region of interest and another region can be automatically set when a predetermined number of characteristic values of the corrected fluorescence image is recorded in the graph generating unit 34. Furthermore, the threshold calculating unit 51 reads out the time variation of the characteristic values recorded in the graph generating unit 34 and generates a histogram of the signal strengths of the characteristic values over time to set a threshold for automatic discrimination between a region of interest and another region.

In the fluoroscopy apparatus 3 according to this modification, the data-item determining unit 61 may count the recording time for the characteristic values of the corrected fluorescence images by the graph generating unit 34, and, when the recording time equals a predetermined time, may send an instruction regarding the timing for setting a threshold for discrimination between a region of interest and another region to the threshold calculating unit 51.

In this way, the threshold for discrimination between the region of interest and another region can be automatically set upon recording the characteristic values in the characteristic-value recording unit at a predetermined time.

Second Modification

Next, a second modification of the fluoroscopy apparatus 2 according to the second embodiment will be described.

A fluoroscopy apparatus 4 according to this modification differs from the fluoroscopy apparatus 2 according to the second embodiment in that the timing for setting a threshold for discrimination between a region of interest and another region is determined on the basis of a graph generated by the graph generating unit 34.

Figure 13:
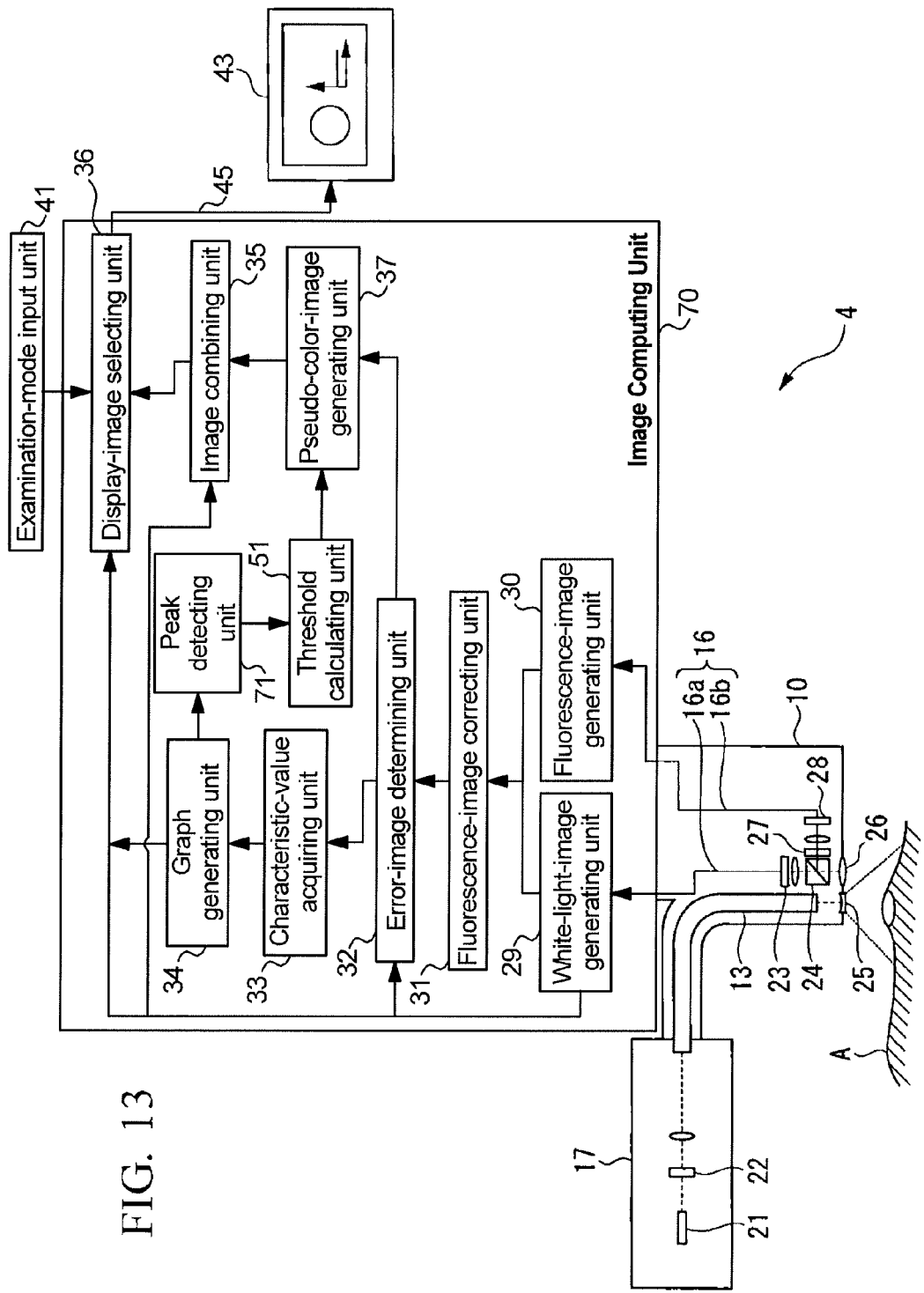
{FIG. 13}

As illustrated in FIG. 13, an image computing unit 70 of the fluoroscopy apparatus 4 according to this modification includes a peak detecting unit 71.

The peak detecting unit 71 reads out a graph of the time variation of the characteristic values generated by the graph generating unit 34, generates a histogram of the signal strengths of the characteristic values over time, and, when two peaks appear in the histogram, sends an instruction regarding the timing for setting a threshold for discrimination between a region of interest and another region to the threshold calculating unit 51.

In this way, when two peaks appear in the histogram of the signal strengths of the characteristic values over time, i.e., when an affected region exists in the examination region, a threshold for discrimination between a region of interest and another region can be automatically set.

The embodiments of the present invention have been described in detail above with reference to the drawings. The specific configurations are not limited to these embodiments, and various modifications in the design may be included in the present invention without departing from the scope thereof.

For example, in the embodiments, examples of the fluoroscopy apparatus according to the present invention being applied to an endoscopic apparatus have been described. Instead, the fluoroscopy apparatus according to the present invention may be applied to a microscope, etc.

In the embodiments, white light is used as illumination light. The illumination light is not limited to white light, however, and other types of light, such as reflected excitation light, may be used.

The white-light-image generating unit 29 is described as generating a white-light image from light reflected at the subject A. Instead, a return-light image may be generated from returning light, such as autofluorescence of the subject A.

The fluorescence-image correcting unit 31 is described as dividing the luminance value of each pixel in a fluorescence image by the luminance value of each pixel in a white-light image. Instead, the signal strength of each pixel in a fluorescence image may be divided by the signal strength of each corresponding pixel in a white-light image for one of the R, G, and B components to generate a corrected fluorescence image.

Reference Signs List

1, 2, 3, 4 fluoroscopy apparatus endoscope
10 light-source device (light source unit)
20, 50, 60, 70 image computing unit
29 white-light-image generating unit (return-light-image generating unit)
30 fluorescence-image generating unit
31 fluorescence-image correcting unit (image correcting unit)
32 error-image determining unit (error determining unit)
33 characteristic-value acquiring unit
34 graph generating unit (characteristic-value recording unit)
35 image combining unit
36 display-image selecting unit
37 pseudo-color-image generating unit (discriminating unit)
38 threshold setting unit (threshold determining unit)
41 examination-mode input unit
42 threshold input unit (signal-strength input unit)
43 monitor (characteristic-value display unit)
51 threshold calculating unit (threshold determining unit)
52 automatic threshold-calculation input unit (threshold setting instruction unit)
61 data-item determining unit
71 peak detecting unit
A subject

The invention claimed is:

1. A fluoroscopy apparatus comprising:
a light source unit configured to generate illumination light and excitation light that are radiated onto an imaging subject;
a fluorescence-image generating unit configured to generate a fluorescence image by imaging fluorescence generated at the imaging subject as a result of being irradiated with the excitation light from the light source unit;
a return-light-image generating unit configured to acquire returning light from the imaging subject irradiated with illumination light from the light source unit and generate a return-light image;
an image correcting unit configured to generate a corrected fluorescence image by dividing the signal strengths of pixels in the fluorescence image generated by the fluorescence-image generating unit by signal strengths of pixels in the return-light image generated by the return-light-image generating unit;
a characteristic-value extracting unit configured to extract a characteristic value of the corrected fluorescence image generated by the image correcting unit;
a threshold determining unit configured to determine a threshold for discrimination between a region of interest and another region of the corrected fluorescence image using a history of characteristic values of the corrected fluorescence image extracted by the characteristic-value extracting unit; and
a discriminating unit configured to discriminate between the region of interest and another region in the corrected fluorescence image on the basis of the threshold determined by the threshold determining unit.

2. The fluoroscopy apparatus according to claim 1, wherein the characteristic-value extracting unit extracts the maximum value of signal strengths of the corrected fluorescence image as a characteristic value.

3. The fluoroscopy apparatus according to claim 1, wherein characteristic-value extracting unit extracts, as the characteristic value, a signal strength corresponding to a cumulative value of the signal strengths of the pixels in the corrected fluorescence image.

4. The fluoroscopy apparatus according to claim 1, further comprising:
a characteristic-value recording unit configured to record a time variation of the characteristic values extracted by the characteristic-value extracting unit;
a characteristic-value display unit configured to display the time variation of the characteristic values recorded in the characteristic-value recording unit; and
a signal-strength input unit configured to receive a signal strength to serve as a reference for the time variation of the characteristic values displayed on the characteristic-value display unit,
wherein the threshold determining unit sets the signal strength input to the signal-strength input unit as the threshold.

5. The fluoroscopy apparatus according to claim 1, further comprising:
a characteristic-value recording unit configured to record a time variation of the characteristic values extracted by the characteristic-value extracting unit; and
a threshold setting instruction unit configured to instruct a timing for setting the threshold,
wherein the threshold determining unit sets the threshold on the basis of the time variation of the characteristic values recorded in the characteristic-value recording unit upon reception of an instruction from the threshold setting instruction unit.

6. The fluoroscopy apparatus according to claim 1, further comprising:
a characteristic-value recording unit configured to record a time variation of the characteristic values extracted by the characteristic-value extracting unit,
wherein the threshold determining unit sets the threshold on the basis of the time variation of the characteristic values recorded in the characteristic-value recording unit upon recording the characteristic values in the characteristic-value recording unit at a predetermined time.

7. The fluoroscopy apparatus according to claim 5, wherein the threshold determining unit generates a histogram of the signal strengths of the characteristic values from the time variation of the characteristic values recorded in the characteristic-value recording unit, sets the maximum signal strength in the histogram as the threshold when the number of peaks in the histogram is one, and, when the number of peaks is two or more, sets a signal strength at a value between the largest signal strength peak and the smallest signal strength peak as the threshold.

8. The fluoroscopy apparatus according to claim 7, wherein, when the histogram has two peaks, the threshold determining unit sets a signal strength between the peaks as the threshold.

9. The fluoroscopy apparatus according to claim 1, further comprising:
an error determining unit configured to detect the signal strengths of the pixels in the return-light image acquired by the return-light-image generating unit and perform error determination when the number of pixels having a saturated signal strength is larger than or equal to a predetermined number of pixels.

10. The fluoroscopy apparatus according to claim 1, further comprising:
an error determining unit configured to detect the signal strengths of the pixels in the corrected fluorescence image generated by the image correcting unit and perform error determination when the number of pixels having a saturated signal strength is larger than or equal to a predetermined number of pixels.

11. The fluoroscopy apparatus according to claim 9, wherein, when the error determining unit performs error determination, the characteristic-value extracting unit interrupts the extraction of the characteristic values.

12. The fluoroscopy apparatus according to claim 6, wherein the threshold determining unit generates a histogram of the signal strengths of the characteristic values from the time variation of the characteristic values recorded in the characteristic-value recording unit, sets the maximum signal strength in the histogram as the threshold when the number of peaks in the histogram is one, and, when the number of peaks is two or more, sets a signal strength at a value between the largest signal strength peak and the smallest signal strength peak as the threshold.

13. The fluoroscopy apparatus according to claim 12, wherein, when the histogram has two peaks, the threshold determining unit sets a signal strength between the peaks as the threshold.

14. The fluoroscopy apparatus according to claim 10, wherein, when the error determining unit performs error determination, the characteristic-value extracting unit interrupts the extraction of the characteristic values.

* * * * *